(12) United States Patent
Ganapati et al.

(10) Patent No.: US 10,473,911 B2
(45) Date of Patent: *Nov. 12, 2019

(54) SIMULTANEOUS VISIBLE AND FLUORESCENCE ENDOSCOPIC IMAGING

(71) Applicant: Verily Life Sciences LLC, South San Francisco, CA (US)

(72) Inventors: Vidya Ganapati, Oakland, CA (US); Eden Rephaeli, Mountain View, CA (US); Daniele Piponi, Oakland, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/393,575

(22) Filed: Apr. 24, 2019

(65) Prior Publication Data

US 2019/0250394 A1   Aug. 15, 2019

Related U.S. Application Data

(63) Continuation of application No. 15/411,221, filed on Jan. 20, 2017.

(51) Int. Cl.
*A61B 6/00* (2006.01)
*G02B 23/24* (2006.01)
(Continued)

(52) U.S. Cl.
CPC ...... *G02B 23/2469* (2013.01); *A61B 1/00009* (2013.01); *A61B 1/043* (2013.01);
(Continued)

(58) Field of Classification Search
CPC ............ G02B 23/2469; G02B 23/2484; A61B 1/063; A61B 1/0638; A61B 1/00009;
(Continued)

(56) References Cited

U.S. PATENT DOCUMENTS 6,293,911 B1 * 9/2001 Imaizumi ........... A61B 1/00009
600/160
6,899,675 B2 * 5/2005 Cline ................. A61B 1/00009
600/109
(Continued)

FOREIGN PATENT DOCUMENTS

EP   1 759 628 A1   3/2007

OTHER PUBLICATIONS

US 6,692,429 B1, 02/2004, Imaizumi et al. (withdrawn)
(Continued)

*Primary Examiner* — Howard D Brown, Jr.
(74) *Attorney, Agent, or Firm* — Christensen O'Connor Johnson Kindness PLLC (57) ABSTRACT

An endoscope apparatus includes a fiber optic cable with a proximal end and a distal end opposite the proximal end. The endoscope apparatus also includes a light source optically coupled to the proximal end of the fiber optic cable to emit visible light and excitation light into the fiber optic cable for output from the distal end. The light source is configured to emit both the visible light and the excitation light simultaneously, and a wavelength of the excitation light is outside a wavelength spectrum of the visible light. An image sensor is configured to receive a reflection of the visible light as reflected visible light.

18 Claims, 8 Drawing Sheets

(51) Int. Cl.
  *G01N 21/64* (2006.01)
  *H04N 5/225* (2006.01)
  *A61B 1/04* (2006.01)
  *A61B 1/06* (2006.01)
  *A61B 1/07* (2006.01)
  *A61B 1/00* (2006.01)
  *A61B 1/045* (2006.01)
  *A61B 1/05* (2006.01)

(52) U.S. Cl.
  CPC ............... *A61B 1/045* (2013.01); *A61B 1/05* (2013.01); *A61B 1/063* (2013.01); *A61B 1/0638* (2013.01); *A61B 1/07* (2013.01); *G01N 21/6456* (2013.01); *G02B 23/2484* (2013.01); *H04N 5/2256* (2013.01); *A61B 1/0005* (2013.01); *G01N 2021/6471* (2013.01); *H04N 2005/2255* (2013.01)

(58) Field of Classification Search
  CPC ........... A61B 1/05; A61B 1/045; A61B 1/043; A61B 1/07; A61B 1/0005; G01N 21/6456; G01N 2021/6471; H04N 2005/2255; H04N 5/2256
  See application file for complete search history.

(56) References Cited

U.S. PATENT DOCUMENTS

| | | | |
|---|---|---|---|
| 7,172,553 B2 * | 2/2007 | Ueno | A61B 1/00009 600/109 |
| 8,498,695 B2 | 7/2013 | Westwick et al. | |
| 8,629,394 B2 * | 1/2014 | Madokoro | H01J 37/153 250/306 |
| 9,175,831 B2 * | 11/2015 | Yamano | A61B 1/0646 |
| 9,345,389 B2 * | 5/2016 | Nie | A61B 1/00174 |
| 9,778,206 B2 * | 10/2017 | Honda | G01N 21/8851 |
| 2003/0048940 A1 * | 3/2003 | Onoyama | G01N 21/95607 382/149 |
| 2004/0264760 A1 * | 12/2004 | Ishikawa | G01N 21/95607 382/145 |
| 2006/0098863 A1 * | 5/2006 | Ishikawa | G01N 21/95607 382/149 |
| 2007/0053580 A1 * | 3/2007 | Ishikawa | G06T 7/001 382/149 |
| 2008/0239070 A1 * | 10/2008 | Westwick | A61B 1/045 348/68 |
| 2009/0244521 A1 * | 10/2009 | Yazdanfar | G01N 21/6456 356/73 |
| 2010/0286529 A1 | 11/2010 | Carroll et al. | |
| 2011/0270092 A1 * | 11/2011 | Kang | A61B 5/0071 600/476 |
| 2016/0022126 A1 * | 1/2016 | Ramesh | H04N 5/332 600/109 |
| 2016/0062103 A1 * | 3/2016 | Yang | G02B 23/2461 250/552 |
| 2018/0210188 A1 * | 7/2018 | Ganapati | G02B 23/2469 |

OTHER PUBLICATIONS

International Search Report and Written Opinion from the International Searching Authority dated May 28, 2018, for International Application No. PCT/US2018/012388, filed Jan. 4, 2018, 12 pages.

\* cited by examiner

$P_r = X_1 QE_{830,r} T_{830,notch} + Y_1 QE_{visible,r} T_{visible,notch} + Z_1 QE_{805,r} T_{805,notch} + N_1$ $P_g = X_2 QE_{830,g} T_{830,notch} + Y_2 QE_{visible,g} T_{visible,notch} + Z_2 QE_{805,g} T_{805,notch} + N_2$ $P_b = X_3 QE_{830,b} T_{830,notch} + Y_3 QE_{visible,b} T_{visible,notch} + Z_3 QE_{805,b} T_{805,notch} + N_3$ $P_c$ denotes the photo-charge at the RGB pixels, $c$ denotes the pixel (Red, Green, or Blue)

$QE_{wavelength,c}$ are the quantum efficiencies of the different wavelengths for color pixel $c$ $X_i$ denotes the photons at 830 nm (Poisson random variable)

$Y_i$ denotes the photons at the visible wavelength (Poisson random variable)

$Z_i$ denotes the photons are 805 nm (Poisson random variable)

$N_i$ denotes the read noise of the image sensor (Gaussian random variable)

$T_{wavelength,notch}$ is the transmission of the notch filter at each wavelength

FIG. 3A $P_r = X_1 QE_{830,r} T_{830,notch} + Y_1 QE_{visible,r} T_{visible,notch} + Z_1 QE_{805,r} T_{805,notch} + N_1$
$P_g = X_2 QE_{830,g} T_{830,notch} + Y_2 QE_{visible,g} T_{visible,,notch} + Z_2 QE_{805,g} T_{805,notch} + N_2$
$P_b = X_3 QE_{830,b} T_{830,notch} + Y_3 QE_{visible,b} T_{visible,notch} + Z_3 QE_{805,b} T_{805,notch} + N_3$ We assume $E[X_1] = E[X_2] = E[X_3] = X$, $E[Y_1] = E[Y_2] = E[Y_3] = Y$, $E[Z_1] = E[Z_2] = E[Z_3] = Z$.

We want to estimate $X$, $Y$, and $Z$ from a measurement of $P_r$, $P_g$, and $P_b$. Denote the estimates of $X$, $Y$, $Z$ as $\hat{X}$, $\hat{Y}$, $\hat{Z}$.

$$Q = \begin{bmatrix} QE_{830,r} T_{830,notch} & QE_{visible,r} T_{visible,notch} & QE_{805,r} T_{805,notch} \\ QE_{830,g} T_{830,notch} & QE_{visible,g} T_{visible,notch} & QE_{805,g} T_{805,notch} \\ QE_{830,b} T_{830,notch} & QE_{visible,b} T_{visible,notch} & QE_{805,b} T_{805,notch} \end{bmatrix}, \quad P = \begin{bmatrix} P_r \\ P_g \\ P_b \end{bmatrix}, \quad \hat{X} = \begin{bmatrix} \hat{X} \\ \hat{Y} \\ \hat{Z} \end{bmatrix}$$

$\Gamma = \alpha I$, where $I$ is the identity matrix and $\alpha$ is a regularization constant.
We estimate $X$, $Y$, and $Z$ with $L_2$ regularization:
$Q^L = (Q^T Q + \Gamma^T \Gamma)^{-1} Q^T$ $\hat{X} = Q^L P$

FIG. 3B

$$\text{var}(P_r) = X(QE_{830,r}T_{830,notch})^2 + Y(QE_{visible,r}T_{visible,notch})^2 + Z(QE_{805,r}T_{805,notch})^2 + \text{var}(N_1)$$
$$\text{var}(P_g) = X(QE_{830,g}T_{830,notch})^2 + Y(QE_{visible,g}T_{visible,notch})^2 + Z(QE_{805,g}T_{805,notch})^2 + \text{var}(N_2)$$
$$\text{var}(P_b) = X(QE_{830,b}T_{830,notch})^2 + Y(QE_{visible,b}T_{visible,notch})^2 + Z(QE_{805,b}T_{805,notch})^2 + \text{var}(N_3)$$

$$\text{var}(\hat{X}) = (Q^L_{11})^2 \text{var}(P_r) + (Q^L_{12})^2 \text{var}(P_g) + (Q^L_{13})^2 \text{var}(P_b)$$

$$\text{var}(\hat{Y}) = (Q^L_{21})^2 \text{var}(P_r) + (Q^L_{22})^2 \text{var}(P_g) + (Q^L_{23})^2 \text{var}(P_b)$$

$$\text{var}(\hat{Z}) = (Q^L_{31})^2 \text{var}(P_r) + (Q^L_{32})^2 \text{var}(P_g) + (Q^L_{33})^2 \text{var}(P_b)$$

$$SNR_x = X/\sqrt{(\text{var}(\hat{X}))}$$
$$SNR_y = Y/\sqrt{(\text{var}(\hat{Y}))}$$
$$SNR_z = Z/\sqrt{(\text{var}(\hat{Z}))}$$

SIMULTANEOUS VISIBLE AND FLUORESCENCE ENDOSCOPIC IMAGING

CROSS-REFERENCE TO RELATED APPLICATIONS

This application is a continuation of U.S. application Ser. No. 15/411,221, filed on Jan. 20, 2017, the contents of which are incorporated herein by reference.

TECHNICAL FIELD

This disclosure relates generally to endoscope imaging.

BACKGROUND INFORMATION

Endoscopy allows a physician to view organs and cavities internal to a patient using an insertable instrument. This is a valuable tool for making diagnoses without needing to guess or perform exploratory surgery. The insertable instruments, sometimes referred to as endoscopes or borescopes, have a portion, such as a tube, that is inserted into the patient and positioned to be close to an organ or cavity of interest.

Endoscopes first came into existence in the early 1800's, and were used primarily for illuminating dark portions of the body (since optical imaging was in its infancy). In the late 1950's, the first fiber optic endoscope capable of capturing an image was developed. A bundle of glass fibers was used to coherently transmit image light from the distal end of the endoscope to a camera. However, there were physical limits on the image quality this seminal imaging endoscope was able to capture: namely, the number of fibers limited the resolution of the image, and the fibers were prone to breaking.

Now endoscopes are capable of capturing high-resolution images, as endoscopes use various modern image processing techniques to provide the physician with as natural a view as possible. However, sometimes it may be desirable to see contrast between organs imaged. For instance, some cancers look very similar to surrounding healthy tissue.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system and method for simultaneous visible and fluorescent endoscopic imaging are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Endoscopes are devices physicians use to view inside of patients without the need to perform exploratory surgery. In general, endoscopes are imaging devices with insertion tubes that are inserted into a patient through small incisions. The imaging device provides views from a tip ("distal end") of the insertion tube and displays the view, for example, on a monitor for the physician. The distal end may be opposite the hand-held portion ("proximal end") of the endoscope. The imaging system may provide a view of an area of interest to the viewer. The color of an object imaged depends on the spectrum of the illumination light source, as well as the object's own spectral reflectance.

Indocyanine Green (ICG) is a dye that bind to proteins in the blood plasma. When pumped with 805 nm light, ICG fluoresces with a peak wavelength at 830 nm. ICG can be injected into the bloodstream, and during surgery, the ICG fluorescence can be imaged to show blood perfusion and vasculature. In endoscopic surgery, the surgeon inserts an endoscope (with a camera and illumination source at the distal end of the endoscope) to image the surgical area of interest in real-time. This disclosure may help solve the problem of obtaining a fluorescence image to show the spatial distribution of the ICG, at the same time as obtaining a regular visible reflectance image, in real-time. The ICG image may provide contrast information that a surgeon can use to better tell the difference between various bodily structures.

This disclosure provides embodiments of an endoscope that may have two discrete laser sources at the proximal end, and a camera at the distal end (the end inserted into the surgical region). A fiber optic cable may optically transmit light from the discrete sources at the proximal end to the distal end. The disclosure may also include a connection from the endoscope to a computer (either internal or external to the endoscope), and the endoscope system includes software that processes the data output from the endoscope image sensor and sends the data to a computer monitor display. The endoscope image sensor may employ a conventional Bayer filter pattern, such that each pixel records an image charge corresponding to red, green, or blue light. On top of the Bayer filter may be a notch filter.

The two discrete laser sources may be an 805 nm laser and a visible wavelength laser. The notch filter may block almost all light at 805 nm wavelength but let light at other wavelengths through. Both the 805 nm laser (the "excitation" laser) and the visible wavelength laser operate simultaneously. The 805 nm laser may cause the ICG dye in the surgical area of interest to fluoresce around 830 nm, and the visible wavelength laser is reflected by the organs in the surgical area. Photons of three wavelength ranges (visible, 805 nm, and 830 nm) may impinge on the camera, but almost all the 805 nm photons are blocked by the notch filter. The three color pixels, red, green, and blue, each have different quantum efficiencies for the three different wavelength ranges. Thus, the responses by the red, green, and blue pixels may be independent linear combinations of the number of photons at each of the three wavelengths of light. The values recorded by the red, green, and blue pixels are sent to the processor, and the software package on the processor/computer uses regularized inversion to computationally determine (from neighboring red, green, and blue pixel values) what the intensity values are for the fluorescent photons and the visible reflected photons. The software may employ knowledge of the visible laser wavelength to convert the recorded red, green, and blue pixel intensity values to image data with the highest possible signal-to-noise ratio. The intensity values for the fluorescent photons and the visible reflected photons are sent to the display, which may display a black and white image for the visible reflectance intensity values (the red, green, and blue pixels of the display are equally scaled by the visible reflectance intensity), and a green overlay for the fluorescence intensity values (a value proportional to the fluorescence intensity may be added to the value for the green display pixel). However, in other embodiments, a full color image may be formed with a fluorescence overlay of a color not commonly encountered in the human body (e.g., florescent orange).

One advantage of the present disclosure is that no additional hardware (such as extra cameras, beam splitters, or image sensors) is needed to record images at two different wavelengths. A camera and image sensor with a Bayer filter can be used. The frame rate of the camera is maintained, and the recorded images at the two different wavelengths are automatically registered to each other.

It is worth noting different fluorophore and excitation laser wavelengths may be used. Moreover an image sensor with a fourth color pixel (such as a near-infrared pixel), which causes there to be four equations in the software algorithm, but the same regularized inversion matrix can be used. Additionally, there may be multiple cameras in the endoscope (for example, for stereo imaging), but each camera may separately have the functionality of simultaneous fluorescence and visible imaging.

Figures 1A, 1B:
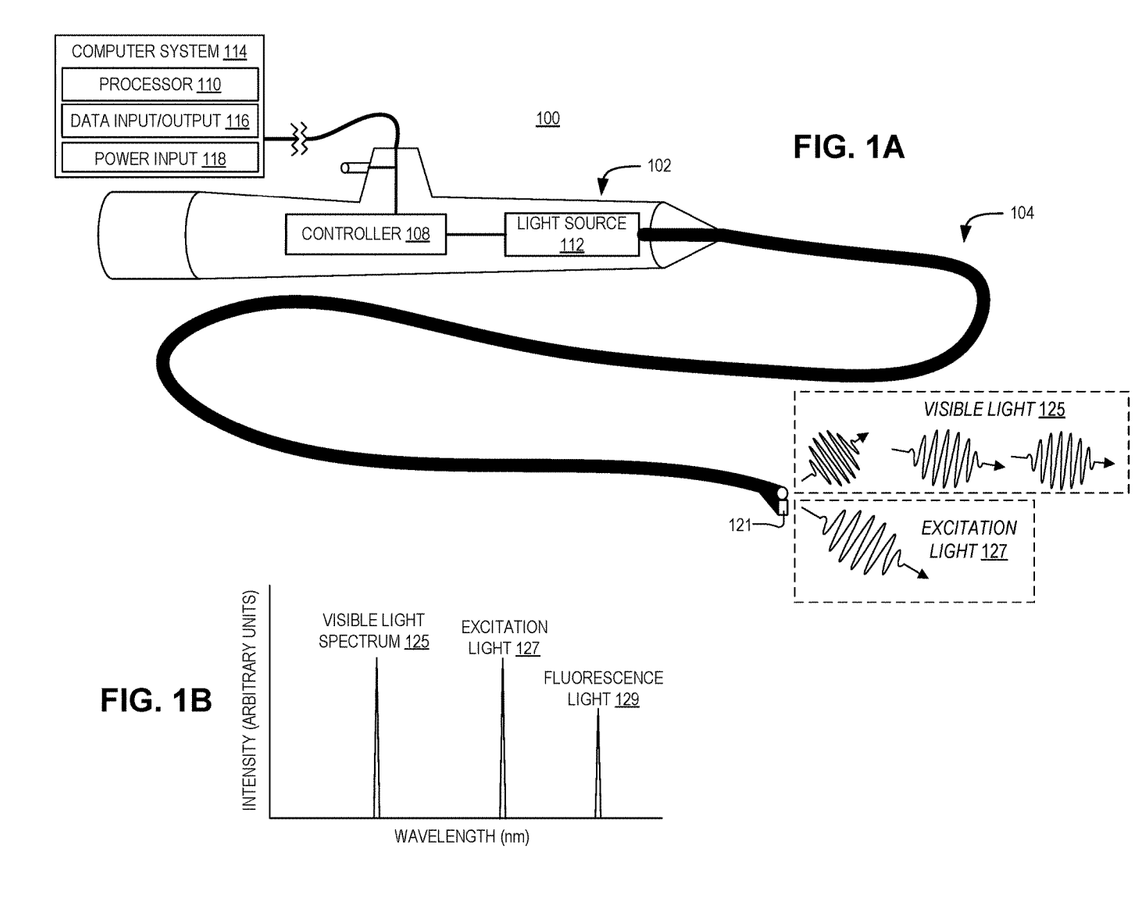
FIG. 1A is an illustration of an endoscope system, in accordance with an embodiment of the disclosure.
FIG. 1B shows an endoscope emission spectrum and a corresponding fluorescence emission spectrum, in accordance with an embodiment of the disclosure.

FIG. 1A is an illustration of an endoscope system 100, in accordance with an embodiment of the disclosure. Endoscope system 100 includes body 102, fiber optic cable 104, light source 112, controller 108, computer system 114 (including processor 110, data input/output 116, and power input 118), and image sensor 121.

Endoscope system 100 includes a proximal end (hand held), and a distal end (end of fiber optic cable 104 opposite the proximal end). Light source 112 is optically coupled to the proximal end of the fiber optic cable 104 to emit visible light 125 and excitation light 127 into fiber optic cable 104 for output from the distal end. Light source 112 is configured to emit both visible light 125 and excitation light 127 simultaneously, and the wavelength of the excitation light 127 is outside the wavelength spectrum of the visible light 125 (see e.g., FIG. 1B). Image sensor 121 is coupled to the distal end of fiber optic cable 104 and positioned to receive a reflection of visible light 125 as reflected visible light. A filter is disposed over image sensor 121, and the filter blocks a majority of excitation light 127 from reaching image sensor 121 while passing a majority of the reflected visible light 125 and fluorescent light to the image sensor 121.

FIG. 1B shows a visible light endoscope emission spectrum 125, an excitation light emission spectrum 127, and a corresponding fluorescence emission spectrum 129, in accordance with an embodiment of the disclosure. In the depicted embodiment, visible spectrum 125 is illustrated as a single wavelength spectrum (or small range of wavelengths); however, in other embodiments visible spectrum 125 may have other emission profiles. As shown the endoscope emits an excitation light spectrum 127 which may be at ~805 nm or another wavelength. In one embodiment excitation light 127 may be higher energy than visible light 125 such as ultraviolet light, depending on the dye used to create the florescence spectrum. In some embodiments the wavelength of excitation light 127 is outside a wavelength spectrum of the visible light 125. As depicted, in response to emitting excitation light 127 with the light source, image sensor 121 receives fluorescence light 129 contemporaneously with the reflected visible light. Fluorescence light 129 has a longer wavelength than excitation light 127. In one embodiment, fluorescence light 129 includes ~830 nm light; but in other embodiments, fluorescence light 129 may be any light with lower energy than excitation light 127. It is worth noting that while in the depicted embodiment excitation light 127 and fluorescence light 129 are relatively monochromatic, in other embodiments the emission profiles of these light sources may be wider so that they include a plurality of wavelengths of light (and may even include a plurality of emission peaks).

Figure 1C:
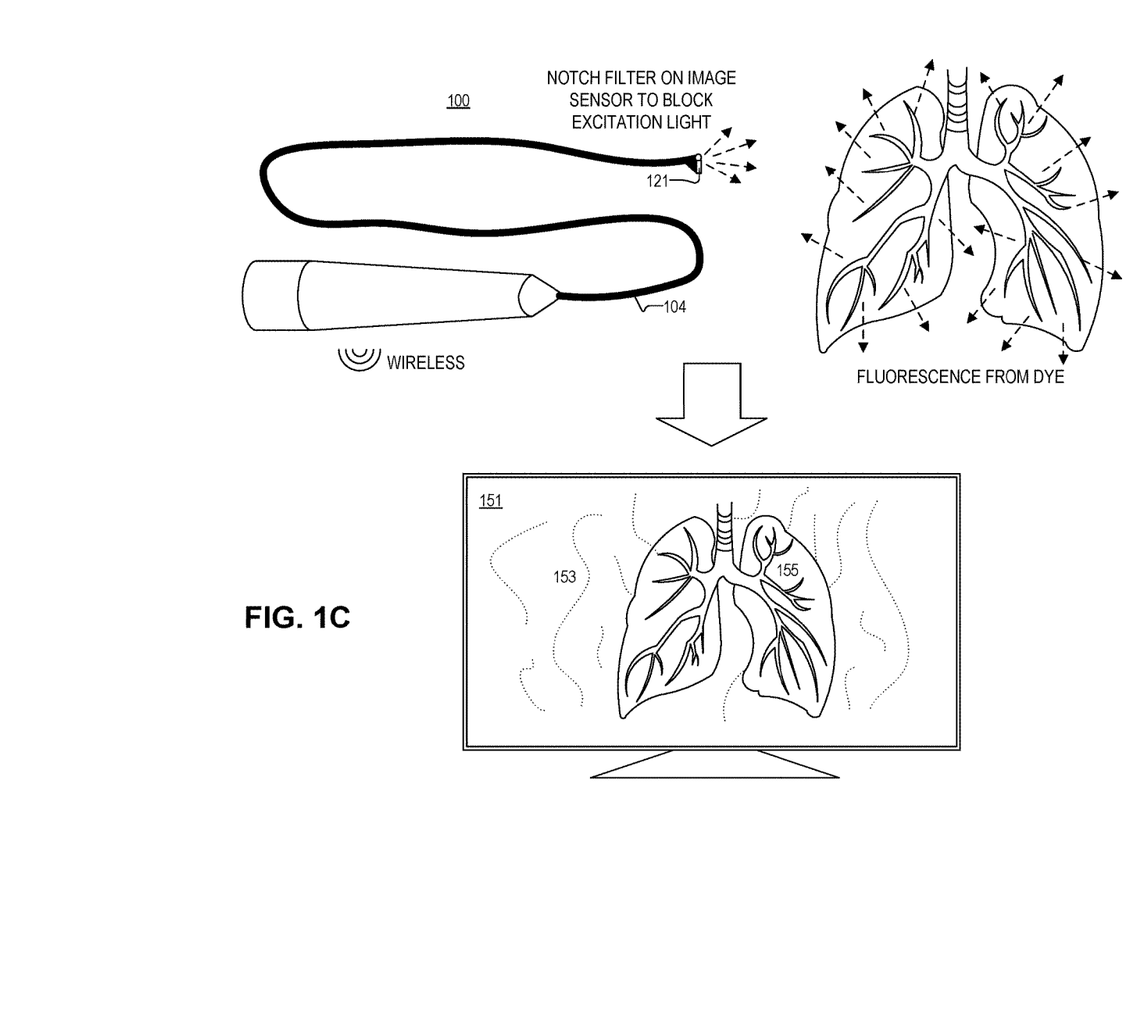
FIG. 1C shows an endoscope emitting visible and excitation light, receiving a fluorescence emission spectrum, and forming a composite image on a screen, in accordance with an embodiment of the disclosure.

FIG. 1C shows endoscope system 100 emitting visible and excitation light, receiving a fluorescence emission spectrum, and forming composite image 151 on a screen, in accordance with an embodiment of the disclosure. In the depicted embodiment, endoscope 100 is simultaneously emitting both visible and excitation light out of the distal end of fiber optic cable 104. The visible and excitation light hits an organ (depicted here as lungs). The lungs have been injected or coated with a fluorescent dye (e.g., molecules, semiconductor particles, etc.). When the excitation light reaches the lungs the dye emits fluorescence light. The reflected visible light and fluorescence light is simultaneously received by image sensor 121, while a notch filter may be used to block the excitation spectrum from being absorbed by image sensor 121 in any significant quantity.

In the depicted embodiment, the reflected visible light and the fluorescence light form combined image data in image sensor 121. The combined image data may be separated in real time by a processing unit (disposed here in endoscope 100) into visible image data and fluorescence image data. In the depicted embodiment, the visible image data is commensurate (e.g., roughly proportional) to the reflected visible light received by image sensor 121 and the fluorescence image data is commensurate to the fluorescence light received by image sensor 121. In one embodiment, separating the combined image data into visible image data and fluorescence image data includes separating the combined image data into red image data corresponding to red photocharge received by image sensor 121, green image data corresponding to green photocharge received by image sensor 121, blue image data corresponding to blue photocharge received by image sensor 121, and florescence image data corresponding to fluorescence photocharge received by image sensor 121. The red image data, the green image data, and the blue image data comprise the visible image data.

Also shown is converting the visible image data and the fluorescence image data into composite image 151. As depicted, the visible image data and the fluorescence image data are displayed simultaneously to produce composite image 151. Composite image 151 includes visible image 153 (dashed line background) and fluorescence image 155 (solid line foreground), where the fluorescence image is overlaid on visible image 153. As previously described, visible image 153 may be black and white or color, and fluorescence image 155 may be green (or the like) overlaid on visible image 153.

Figure 2:
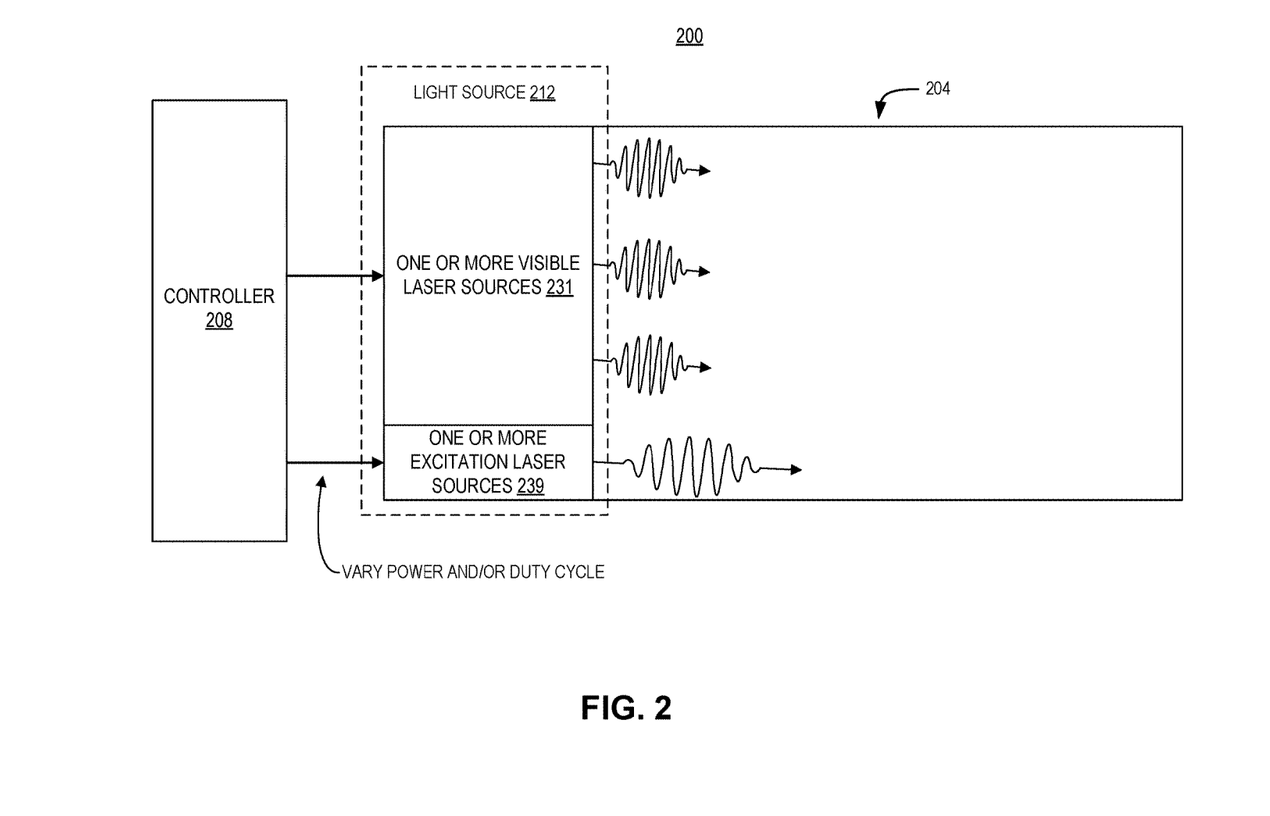
FIG. 2 illustrates an endoscopic light emitter, in accordance with an embodiment of the disclosure.

FIG. 2 illustrates an endoscopic light emitter 200 (including light source 212), in accordance with an embodiment of the disclosure. As shown the visible light is emitted from one or more visible laser sources 231, and the excitation light is emitted from the one or more excitation laser sources 239. The wavelength of the excitation light is longer than the wavelength spectrum of the visible light. The one or more visible laser sources 231 and the one or more excitation laser sources 239 may be a single laser diode capable of emitting a plurality of wavelengths, or may be multiple independent laser sources each emitting a different wavelength of light. As depicted, light source 212 may be optically coupled to fiber optic cable 204 to direct the visible light and the excitation light into a proximal end of fiber optic cable 204. Thus the light is transmitted into fiber optic cable 204, and the light is totally internally reflected within fiber optic cable 204 until it reaches the distal end where it is emitted.

As illustrated, controller 208 is coupled to light source 212 to regulate the output of light source 212. For instance, the controller 208 may be part of the processor system or may be a stand-alone controller to control the output of light source 212. In one embodiment, controller 208 may independently control the intensity of individual laser sources to balance the amount of excitation light and visible image light emitted. In one embodiment, light source 212 may have any number of light sources including lasers and/or light emitting diodes. Further, while the lasers depicted in FIG. 2 emit relatively monochromatic light (e.g., light with a bandwidth of less than 1 nm), in other embodiments, the bandwidth(s) of light source 212 may be larger (on the order of 5 nm or more). In some embodiments, fiber optic cable 204 may include cladding to promote total internal reflection (e.g., the cladding may include a reflective metal, or a material with a lower index of refraction than the bulk of fiber optic cable 204), or contain multiple fibers.

FIGS. 3A-3D illustrate a method of calculating a visible and fluorescence image, in accordance with an embodiment of the disclosure. One of ordinary skill in the art will appreciate that all portions of the method depicted may occur in a processor/controller coupled to, or included in, the endoscope. Moreover the endoscope may communicate to a local or remote processor via wireless or wired communication. In some embodiments, the processor/controller may be a distributed system (for example in embodiments where a lot of data needs to be processed, e.g., high definition video). It is appreciated that the embodiments depicted illustrate a situation where excitation light is 805 nm, and florescence light is 830 nm, but in other embodiments, other wavelengths/dyes may be used.

Figure 3A:
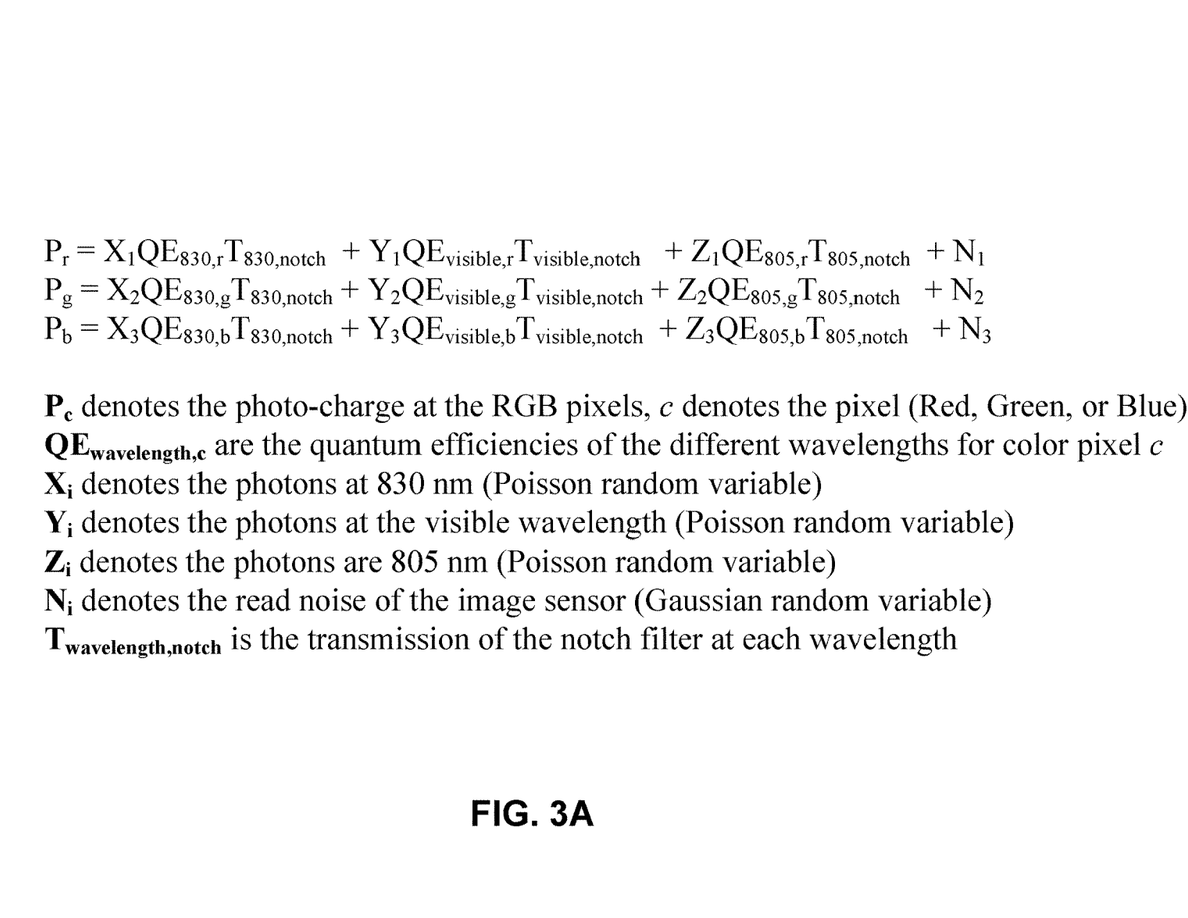
FIGS. 3A-3D illustrate a method of calculating a visible and fluorescence image, in accordance with an embodiment of the disclosure.

FIG. 3A shows part of a method to calculate visible and fluorescence images from an endoscope. As illustrated, an image sensor generates photocharge in its pixels in response to receiving visible (red, green, and blue light), fluorescence light, and a relatively small quantity of excitation light. A processor coupled to the image sensor then separates the photocharge generated into the visible and florescence signal. This is achieved by using known parameters of the image sensor/endoscope system to solve a system of algebraic equations. For example, the various components that make up the red photocharge are known and include $X_1$ (photons absorbed at 830 nm) multiplied by $QE_{830}$ (the quantum efficiency of the image sensor at 830 nm—the fluorescence emission wavelength) and $T_{830,notch}$ (the transmission of 830 nm light through the notch filter). This term is then added to $Y_1$ (visible photons absorbed) multiplied by $Q_{Evisible}$ (the quantum efficiency of the image sensor in the visible wavelength) and $T_{visible,notch}$ (transmission of visible light through the notch filter). This term is then added to $Z_1$ (excitation photons absorbed) multiplied by $QE_{805}$ (the quantum efficiency of the image sensor in the excitation wavelength) and $T_{805,notch}$ (the transmission of excitation light through the notch filter). One of skill in the art will appreciate that this excitation term is ~0 since almost no excitation light will make it through the notch filter. These terms are then added to the noise ($N_1$) of the image sensor. As shown, similar equations are set up for green photocharge ($P_g$) and blue photocharge ($P_b$). The depicted system of equations allow the visible (Y) and fluorescence (X) image signals to be solved for and yield the visible and fluorescence images.

Figure 3B:
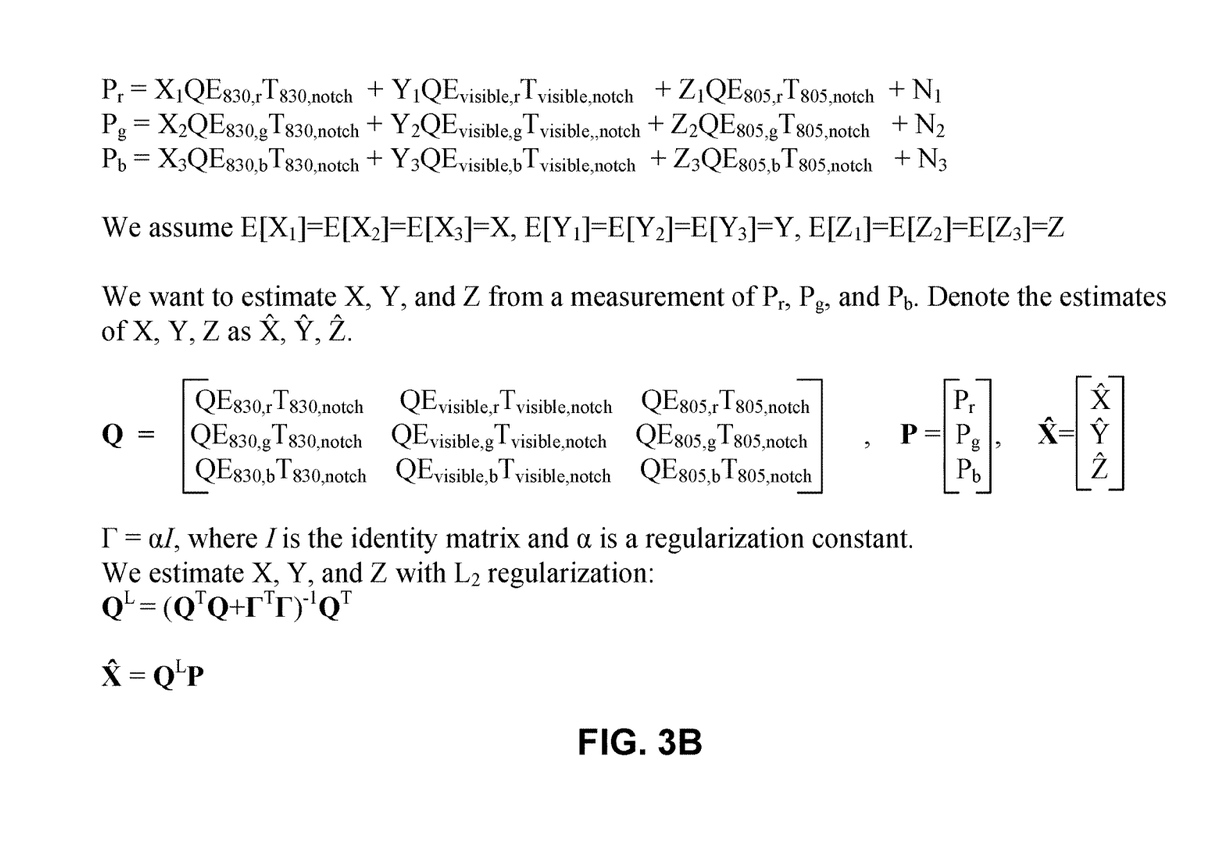

FIG. 3B shows solving the system of equations to obtain the visible and fluorescence signals. FIG. 3B also introduces the concept of regularization in order to stabilize both the matrix and ultimately the visible and florescence images generated. In general, the mathematical operations need to solve for the visible and fluorescence images may introduce unstable conditions in certain situations (e.g., divide by zero, or other very small denominator, as a result of a readout glitch in the image sensor or the like). This may cause image distortion. Accordingly, the system may regularize the output by estimating values for X, Y, and Z. In the depicted embodiment, $\Gamma = \alpha I$, where I is the identity matrix and $\alpha$ is a regularization constant. X, Y, and Z are estimated with L2 regularization such that: $Q^L = (Q^T Q + \Gamma^T \Gamma)^{-1} Q^T$, and thus $\hat{X} = Q^L P$.

Figure 3C:
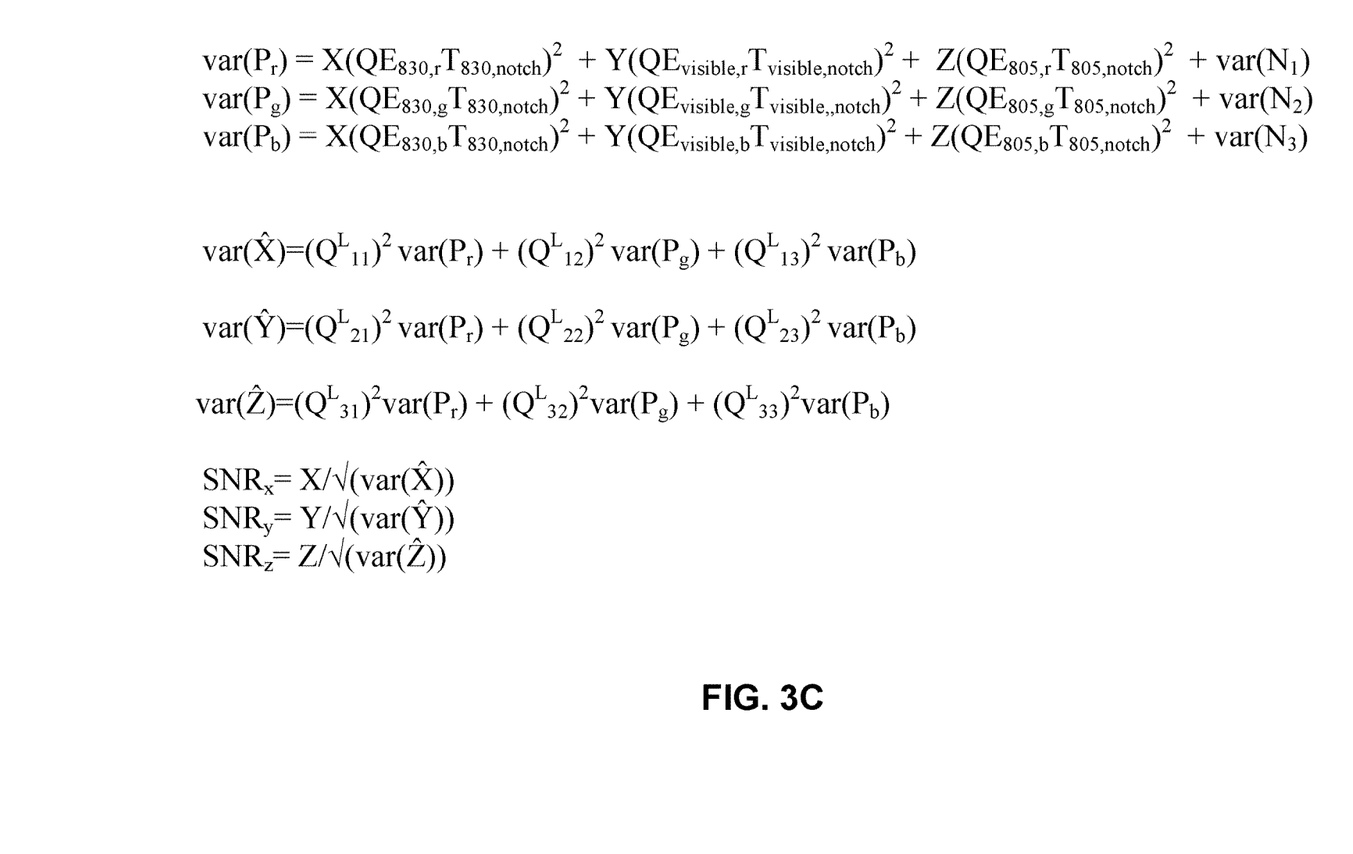

FIG. 3C depicts the mathematical operations to calculate the variance of the photocharge in the image sensor (variance of Pr, Pg, Pb) and consequently the variance in the visible (Y), fluorescence (X), and excitation (Z) image signals (through a similar algebraic matrix operation as discussed above in connection with FIG. 3A). With the variance calculated, the signal to noise ratios (SNR) of X, Y, and Z can be determined. Ideally the system is attempting to maximize the SNR of the X, Y, and Z signals.

Figure 3D:
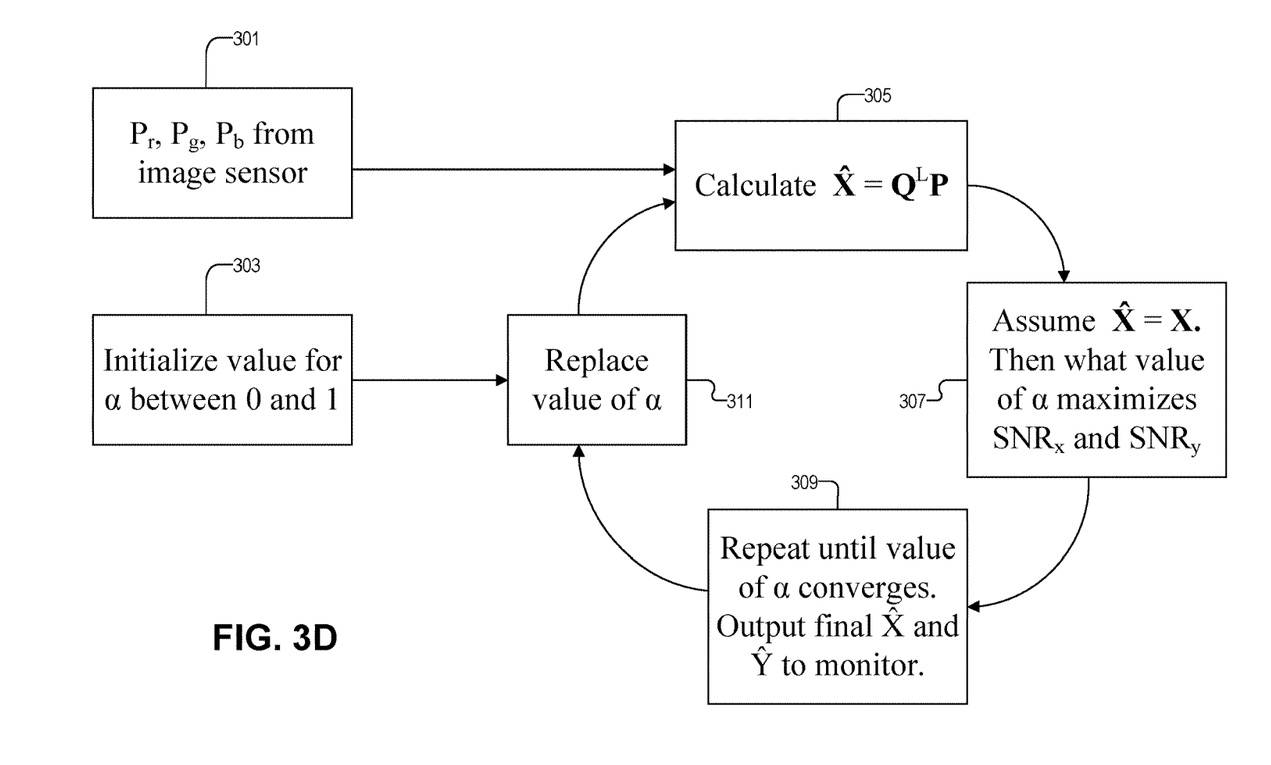

FIG. 3D depicts a method of stabilizing the visible and fluorescence images output from the endoscope image sensor. Block 301 depicts receiving the RGB photocharge from the image sensor. Block 303 depicts initializing a value for the regularization constant ($\alpha$) to stabilize the images output. Block 305 shows calculating $\hat{X} = Q^L P$. Block 307 depicts assuming that $\hat{X} = X$, then calculating the value of $\alpha$ maximizes $SNR_x$ and $SNR_y$. Block 309 illustrates repeating the $\alpha$ calculation until the value of $\alpha$ converges. Then a final $\hat{X}$ and $\hat{Y}$ value are output and monitored. Finally in block 311 the value of $\alpha$ is replaced. Blocks 305-311 repeat themselves indefinitely.

Figure 4:
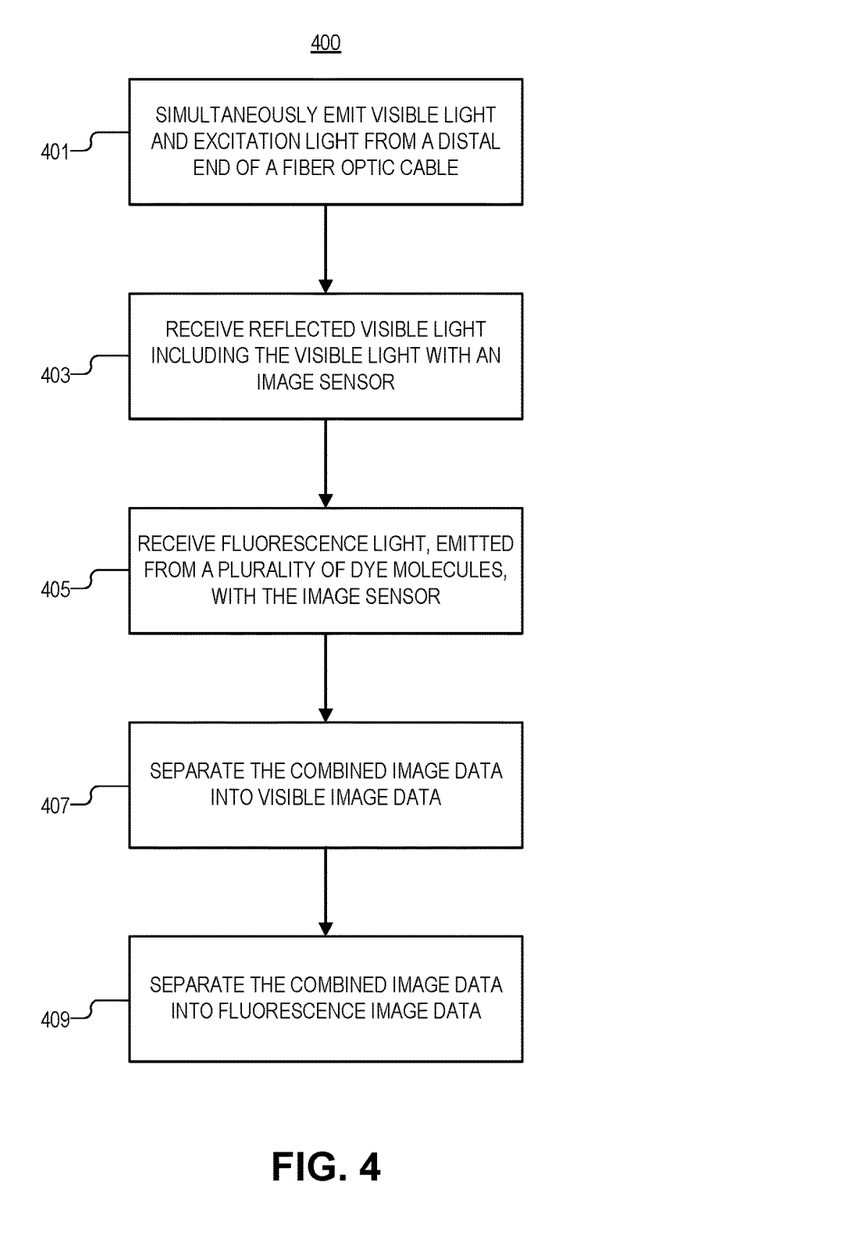
FIG. 4 illustrates a method of medical imaging, in accordance with an embodiment of the disclosure.

FIG. 4 illustrates a method 400 of medical imaging, in accordance with an embodiment of the disclosure. The order in which some or all of process blocks 401-409 appear in method 400 should not be deemed limiting. Rather, one of ordinary skill in the art having the benefit of the present disclosure will understand that some of method 400 may be executed in a variety of orders not illustrated, or even in parallel.

Process block 401 shows simultaneously emitting visible light and excitation light from a distal end of a fiber optic cable of an endoscope. In one embodiment, a wavelength of the excitation light is outside a wavelength spectrum of the visible light (e.g., the excitation light has a longer wavelength than the visible light).

Process block 403 illustrates receiving reflected visible light (including the visible light) with an image sensor. In one embodiment, a majority the excitation light is blocked from being absorbed by the image sensor with a filter. In some embodiments this may be a notch filter, or any other wavelength selective filtering.

Process block 405 depicts receiving fluorescence light, emitted from a plurality of dye molecules, with the image sensor, and the fluorescence light is emitted in response to the plurality of dye molecules absorbing the excitation light. The fluorescence light may have a longer wavelength than the visible or excitation light. The fluorescence light is received by the image sensor contemporaneously with the reflected visible light. The reflected visible light and the fluorescence light form combined image data in the image sensor simultaneously.

Process block 407 shows separating the combined image data into visible image data; the visible image data is commensurate to the reflected visible light received by the image sensor.

Process block 409 illustrates separating the combined image data into fluorescence image data; the fluorescence image data is commensurate to the fluorescence light received by the image sensor. In one embodiment, separating the combined image data into visible image data and fluorescence image data includes separating the combined image data into red image data corresponding to red photocharge absorbed by the image sensor, green image data corresponding to green photocharge absorbed by the image sensor, blue image data corresponding to blue photocharge absorbed by the image sensor, and florescence image data corresponding to fluorescence photocharge absorbed by the image sensor. In some embodiments, to obtain the red green, blue, and florescence photocharge, a Bayer color filter pattern is used, but the Bayer filter does not block the florescence spectrum.

Although depicted elsewhere, in come embodiments a composite image may be formed with the visible image data and the fluorescence image data. The visible image data and the fluorescence image data may be displayed simultaneously to produce the composite image. This allows for a doctor to clearly identify different areas of the body during an operation. The composite image may include a visible image (including the visible image data) and a fluorescence image (including the fluorescence image data). The fluorescence image is overlaid on the visible image. For example if a tumor is florescent but the surrounding tissue is not, the doctor can more easily remove the tumor.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An endoscope apparatus, comprising: a fiber optic cable with a proximal end and a distal end opposite the proximal end;
   a light source optically coupled to the proximal end of the fiber optic cable to emit visible light and excitation light into the fiber optic cable for output from the distal end, wherein the light source is configured to emit both the visible light and the excitation light simultaneously, and wherein a wavelength of the excitation light is outside a wavelength spectrum of the visible light;
   an image sensor configured to receive a reflection of the visible light as reflected visible light and configured to receive fluorescence light generated in response to the excitation light emitted from the light source;
   and a controller coupled to the image sensor to receive combined image data from the image sensor, wherein the combined image data is representative of the reflected visible light and the fluorescence light, and wherein the controller includes logic that when executed by the controller causes the endoscope apparatus to perform operations including: separating the combined image data into visible image data and fluorescence image data;
   and separating the visible image data into at least first color image data corresponding to a first color photocharge and second color image data corresponding to a second color photocharge, wherein the fluorescence image data corresponds to fluorescence photocharge.

2. The endoscope apparatus of claim 1, further comprising a filter disposed over the image sensor, wherein the filter blocks a majority of the excitation light from reaching the image sensor, while passing a majority of the reflected visible light to the image sensor.

3. The endoscope apparatus of claim 2, wherein the light source includes one or more laser sources to emit the visible light and the excitation light, and wherein the wavelength of the excitation light is longer than the wavelength spectrum of the visible light.

4. The endoscope apparatus of claim 3, further comprising color filters disposed over the image sensor and configured to pass the fluorescence light contemporaneously with the reflected visible light to the image sensor, and wherein the fluorescence light has a longer wavelength than the excitation light and is generated in response to the light source emitting the excitation light.

5. The endoscope apparatus of claim 4, wherein the excitation light includes 805 nm light, and the fluorescence light includes 830 nm light.

6. The endoscope apparatus of claim 1, wherein separating the visible image data into at least the first color image data and the second color image data further comprises:
   separating the visible image data into third color image data corresponding to third color photocharge.

7. The endoscope apparatus of claim 6, wherein the controller further includes logic that when executed by the controller causes the endoscope apparatus to perform operations including: employing regularized inversion to determine intensity values for the fluorescent image data and the visible image data;

and forming a composite image with the first color image data, the second color image data, the third color image data, and the fluorescence image data.

8. The endoscope of claim 7, wherein first color image data comprises red image data, the second color image data comprises green image data, and the third color image data comprises blue image data.

9. A method of medical imaging comprising: simultaneously emitting visible light and excitation light from a distal end of a fiber optic cable of an endoscope, wherein a wavelength of the excitation light is outside a wavelength spectrum of the visible light; receiving reflected visible light including the visible light with an image sensor; receiving fluorescence light, emitted from a plurality of dye molecules, with the image sensor, wherein the fluorescence light is emitted in response to the plurality of dye molecules absorbing the excitation light, and wherein the fluorescence light is received by the image sensor contemporaneously with the reflected visible light, and wherein the reflected visible light and the fluorescence light form combined image data in the image sensor;

separating visible image data from the combined image data, wherein the visible image data includes first color image data corresponding to first color photocharge collected in the image sensor, second color image data corresponding to second color photocharge collected in the image sensor, and third color image data corresponding to third color photocharge collected in the image sensor;

and separating fluorescence image data from the combined image data, wherein the fluorescence image data corresponds to fluorescence photocharge collected in the image sensor.

10. The method of claim 9, further comprising blocking a majority the excitation light from being absorbed by the image sensor with a filter.

11. The method of claim 10, wherein the first color image data comprises red image data, the first color photocharge comprises red photocharge, the second color image data comprises green image data, the second color photocharge comprises green photocharge, the third color image data comprises blue image data, and the third color photocharge comprises blue photocharge.

12. The method of claim 9, further comprising forming a composite image with the visible image data and the fluorescence image data, wherein the visible image data and the fluorescence image data are displayed simultaneously to produce the composite image.

13. The method of claim 12, wherein the composite image includes a visible image including the visible image data and a fluorescence image including the fluorescence image data, wherein the fluorescence image is overlaid on the visible image.

14. The method of claim 9, wherein the wavelength of the excitation light is longer than the wavelength spectrum of the visible light, and wherein a wavelength of the fluorescence light is longer than the wavelength of the excitation light.

15. The method of claim 9, further comprising generating the visible light and the excitation light at a proximal end of the fiber optic cable, opposite the distal end of the fiber optic cable, with one or more laser sources, and wherein the visible light and the excitation light are emitted from the distal end.

16. A system for medical imaging, comprising: a fiber optic cable with a distal end and a proximal end opposite the distal end;

a light source optically coupled to the proximal end of the fiber optic cable to emit visible light and excitation light into the fiber optic cable for output from the distal end;

an image sensor coupled to the fiber optic cable to receive reflected visible light and fluorescence light;

and a controller coupled to the light source and the image sensor, wherein the controller includes logic that when executed by the controller causes the system to perform operations including: emitting both the visible light and the excitation light simultaneously from the light source, wherein a wavelength of the excitation light is outside a wavelength spectrum of the visible light;

receiving combined image data from the image sensor; separating visible image data from the combined image data, wherein the visible image data includes first color image data corresponding to first color photocharge, and second color image data corresponding to second color photocharge;

and separating fluorescence image data from the combined image data, wherein the fluorescence image data corresponds to fluorescence photocharge.

17. The system of claim 16, wherein the controller further includes further logic that when executed by the controller causes the system to perform further operations including: controlling one or more laser sources in the light source to simultaneously emit the visible light and the excitation light; and adjusting a power supplied to the one or more laser sources to independently control an intensity of the visible light and the excitation light.

18. The system of claim 16, further comprising an optical filter disposed over the image sensor, wherein the optical filter is a notch filter that blocks a majority of the excitation light from being absorbed by the image sensor.

* * * * *